(12) United States Patent
Reifart et al.

(10) Patent No.: US 6,702,781 B1
(45) Date of Patent: Mar. 9, 2004

(54) ADJUSTABLY STIFFENABLE CONVERTIBLE CATHETER ASSEMBLY

(75) Inventors: Nikolaus Reifart, Eppstein/Taunus (DE); Erik Andersen, Jyllinge (DK); John E. Abele, Concord, MA (US); Sandra G. Tartaglino, Canton, MA (US); Timothy W. Wheeler, Upton, MA (US)

(73) Assignee: Boston Scientific Technology, Inc., Maple Grove, MN (US)

( * ) Notice: Subject to any disclaimer, the term of this patent is extended or adjusted under 35 U.S.C. 154(b) by 1,826 days.

(21) Appl. No.: 08/007,756

(22) Filed: Jan. 22, 1993

Related U.S. Application Data

(63) Continuation of application No. 07/681,805, filed on Apr. 5, 1991, now abandoned.

(51) Int. Cl.[7] ............................................. A61M 29/00
(52) U.S. Cl. ................................... 604/96.01; 606/194
(58) Field of Search ............................ 604/102, 93–96, 604/280, 264, 160, 282, 161; 606/192–195; 128/657, 772

(56) References Cited

U.S. PATENT DOCUMENTS

| | | | |
|---|---|---|---|
| 4,552,554 A | * 11/1985 | Gould et al. | 604/51 |
| 4,748,982 A | * 6/1988 | Horzewski et al. | 604/102 |
| 4,777,951 A | 10/1988 | Cribier et al. | |
| 4,892,519 A | * 1/1990 | Songer et al. | 604/96 |
| 4,944,745 A | * 7/1990 | Sogard et al. | 606/194 |
| 4,960,411 A | * 10/1990 | Buchbinder | 604/96 |
| 4,964,853 A | * 10/1990 | Sugiyama et al. | 604/96 |

OTHER PUBLICATIONS

Letter from the Canadian Intellectual Property Office of Apr. 10, 2003 regarding Canadian application No. 2,082,381.

* cited by examiner

*Primary Examiner*—Manuel Mendez
(74) *Attorney, Agent, or Firm*—Fish & Richardson P.C.

(57) ABSTRACT

A stiffenable balloon catheter assembly capable of being converted from an "over-the-wire" mode with respect to a guidewire extending therethrough to a "rapid-exchange" mode with respect to a guidewire extending therethrough, and vice versa. The catheter has a plurality of lumens, one lumen however, having a side opening with an obstructable galp, the orientation of which, determines the utilization "mode" of the catheter assembly. Stiffening stylets may be adjustably locked into the lumens, depending upon the "mode", to control the stiffness of the catheter assembly during its utilization within a patient.

2 Claims, 3 Drawing Sheets

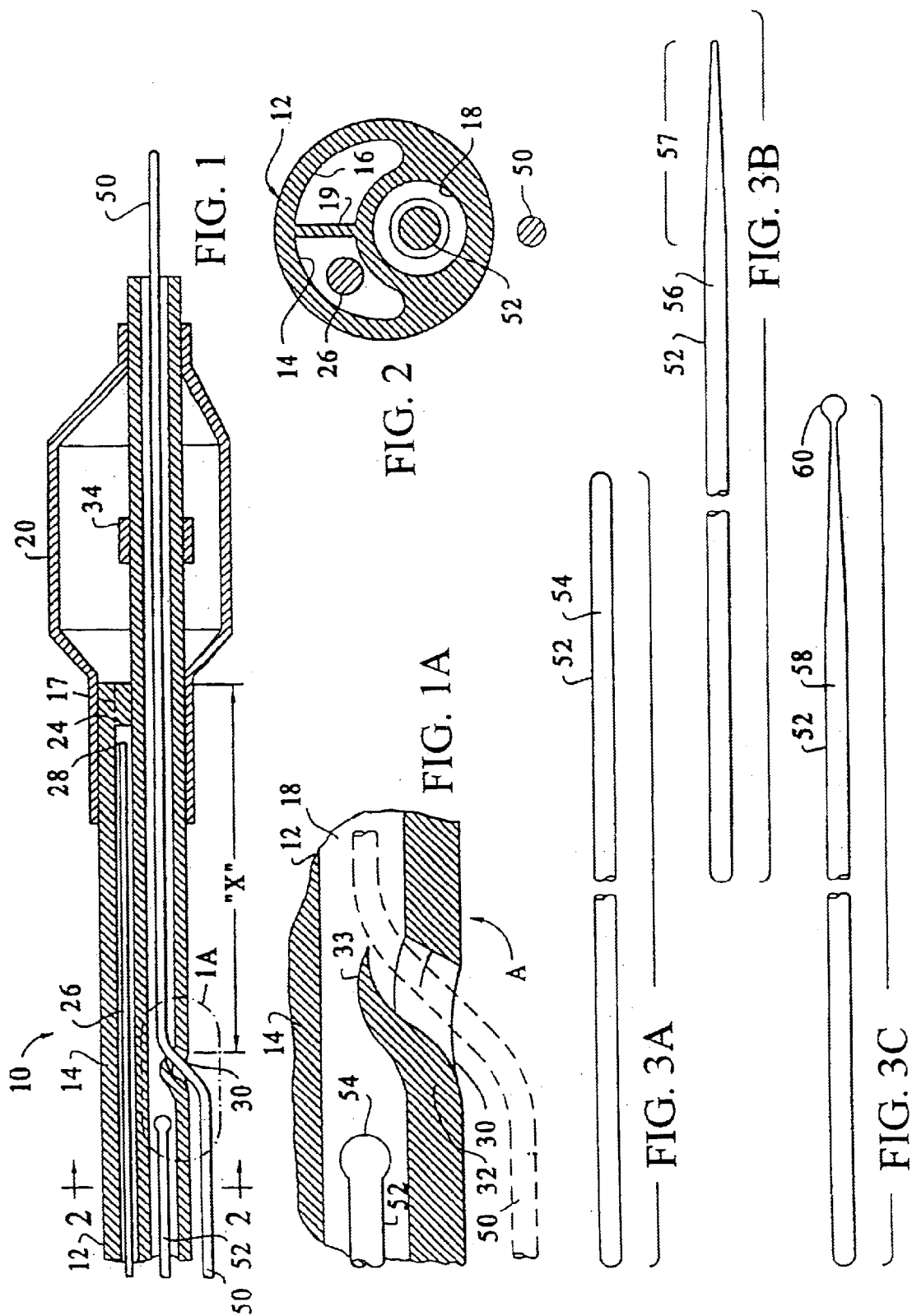

ADJUSTABLY STIFFENABLE CONVERTIBLE CATHETER ASSEMBLY

CROSS-REFERENCE TO RELATED APPLICATION

This is a continuation of application Ser. No. 07/681,805, filed Apr. 5, 1991 now abandoned.

BACKGROUND OF THE INVENTION

1. Field of the Invention

This invention relates to a catheter having a balloon at its distalmost end, and having means for adjustably controlling the stiffness of the catheter shaft, and more particularly to a convertible-type balloon catheter having stiffener means disposed within the catheter.

2. Prior Art

Balloon catheters are utilized for insertion into the human body into lumens therewithin. The catheters are of necessity made of a flexible plastic extrusion such as polyethelene, polyester or polyamide. Advancement and manipulation of a catheter requires a certain stiffness or pushability of the catheter itself, by the physician, without injuring the patient in which the catheter is placed.

A number of approaches have been made, in attempting to provide stiffness to catheters. U.S. Pat. No. 4,964,853 to Sugiyama et al shows a balloon catheter having a braided wire member disposed within the catheter body itself in a mesh-like manner. Mesh is imbedded in the wall of the inner tube. U.S. Pat. No. 4,875,841 to Higgins shows a balloon catheter having a coiled wire arranged within the proximal-most hub, which coiled wire extends in an uncoiled manner within the body of the catheter shaft itself. The coil and the wire itself being co-rotatable so as to provide rotational stiffness to the catheter.

U.S. Pat. No. 4,822,345 to Danforth shows a variable stiffener balloon catheter, for percutaneous transluminal coronary angioplasty procedures. This patent to Danforth shows a method of providing for variable flexibility, by the use of a longitudinally extended balloon arranged along the exterior of the catheter shaft. Pressurization or depressurization of this balloon is effectuated by a syringe, which pressurizably controls the rigidity of the balloon itself. A further embodiment of this concept of Danforth utilizes relatively stiff wires running through channels in the periphery of the catheter, the wires adding the stiffness to the catheter.

The preformed catheter assembly shown in U.S. Pat. No. 4,738,667 to Galloway discloses a sheath which is slideably mounted over the catheter so as to be moved from the proximal to the distal end, to straighten out the distal end during insertion and removal of the catheter from a body. The catheter assembly shown in U.S. Pat. No. 4,737,152 to Alchas shows a stylet or stiffening wire arranged within a lumen connected to the closed distal end of the catheter and also there is a loop on its proximalmost end. The loop is arranged in a rotatable knob to facilitate rotation of the distal end of the catheter while providing stiffness, while the proximal end is turned.

U.S. Pat. No. 4,586,923 issued to Gould et al shows a curving tip catheter having a catheter body which includes a sheath of braided wire having a meshlike configuration positioned around the wall of the tubular body to provide tortional stiffness to the body relative to the flexible tip. In an alternative embodiment, a relatively stiff but bendable inner plastic tubing can be inserted within the tubular body to provide tortional stiffness to that body. In a somewhat similar vein, U.S. Pat. No. 4,516,972 to Sampson shows a guiding catheter having a helically wound ribbon of flexible material embedded within the wall of the catheter, so as to provide tortional rigidity and stiffness.

In yet a further embellishment on the idea of stiffening a balloon catheter, U.S. Pat. No. 4,448,195 to LeVeen et al shows a reinforced balloon catheter which has a guidewire adapted to be inserted for stretching the catheter when it is inserted into a blood vessel to stiffen the catheter and position it. In an alternative arrangement, a braided shell wire reinforcement is used within the braids, which are placed at the beginning and endings of the thinned portion of the catheter. U.S. Pat. No. 4,033,331 to Guss et al, discloses a contour or stiffening wire slideably disposed within a lumen extending substantially the full length of the catheter. Slight retraction of the stiffening wire from the distal end of the lumen permits catheter to assume a predetermined curvature thereat.

It is thus an object of the present invention to provide a catheter having variable stiffness capabilities therewithin. The catheter of the present invention should overcome the problems of the prior art by getting the physician to properly adjust the rigidity or stiffness of the catheter shaft according to the particular situation that warrants it in conjunction with the capability of utilizing the catheter shaft in a convertible manner between a "rapid-exchange" mode and an "over-the-wire" mode.

BRIEF SUMMARY OF THE INVENTION

The present invention comprises a balloon catheter having a catheter shaft with at least three lumens extending from the proximal to the distal ends thereof. The first and second lumens may preferably but not necessarily be of cresent shape in cross-section, and the third lumen is of circular cross-section. At least one of the cresent shaped lumens has a stiffening mandrel extending therethrough. In a preferred embodiment, the third lumen has a side opening arranged relatively close yet proximal to the balloon at the distal end of the catheter assembly.

The balloon on the distal end of the catheter shaft is in fluid communication with one of the cresent shaped lumens. The first shaped lumen has a closed distalmost end, at the proximal end of the balloon.

The third lumen, preferably of circular cross-section, extends from the proximal end of the catheter shaft, and through the balloon, open at its distalmost end at the distal end of the balloon. The third lumen is adapted to receive a guidewire, either through the entire length thereof, or from an opening proximal of the balloon and through to its distalmost end.

In a preferred embodiment, a guidewire is adaptable to enter the third "distal" lumen at its opening at the distalmost end of the catheter and extend through that lumen, through the balloon, and exit out the side opening through the sidewall of the catheter, proximal of the balloon. The side "guidewire" opening of the third lumen being disposed through the wall of the catheter shaft at a location which is also proximal to the distal end of the stiffening mandrel in the first cresent shaped lumen. This rapid exchange mode with a guidewire extending partway through may occur with a stiffening stylet disposed within the third lumen, the stylet extending up to a location adjacent the side opening, from the proximal end of the catheter. This same lumen, a portion of which is utilized for the "rapid-exchange" mode, is utilized in its entire length, for the catheter in its "over-the'wire" mode, where a guidewire enters the distal opening of the third "distal" lumen, and exits at the proximal end of the catheter at the proximal end of that third lumen, through a connector or adaptor.

The present invention thus comprises a multiple lumen catheter (at least three lumens) having proximal and distal ends, the proximal end having a Y-connector thereat for adaptation of inflation devices or control functions, the distal end comprising an inflatable elongated balloon.

A first of the lumens has an elongated stiffening mandrel disposed therein, the lumen being closed at its distalmost end. The stiffening mandrel being preferably made of Nitinol. A second of the lumens extending from the connector, and into the balloon, providing fluid communication therewith. The third of the lumens being preferably circular in cross-section, extending from the connector and through the balloon, and open through the distal tip of the catheter shaft. A "side" orifice being disposed through the wall of the catheter and into the third lumen, just proximal (about 15 to 35 cm) of the balloon. The stiffening mandrel in the first lumen extending distally of the side orifice in the third lumen to the proximal end of the catheter, so as to allow a smoother transition of catheter stiffness when the assembly is utilized in a rapid exchange mode—that is, when a guidewire extends only part way through the third lumen, out through the "side" orifice after entering that lumen distally and to help transmit "push" on the catheter shaft from'its proximal end. The same lumen therefore, in the same catheter, functioning as a lumen for an "over-the-wire" mode, as well as a "rapid-exchange-wire" mode, using part of the lumen for a guidewire and part of that lumen for catheter stiffening assistance.

BRIEF DESCRIPTION OF THE DRAWINGS

The objects and advantages of the present invention will become more apparent when viewed in conjunction with the following drawings, in which:

FIG. 1 is a sectional side-elevational view of the distal portion of a catheter assembly constructed according to the principles of the present invention;

FIG. 1a is an enlarged view of the "side opening" shown in cross-section in FIG. 1;

FIG. 2 is a cross-sectional view taken along the lines II—II of FIG. 1;

FIGS. 3a, 3b, and 3c are side-elevational views of stiffening mandrels contemplated with this catheter assembly;

DESCRIPTION OF THE PREFERRED EMBODIMENTS

Figure 4:
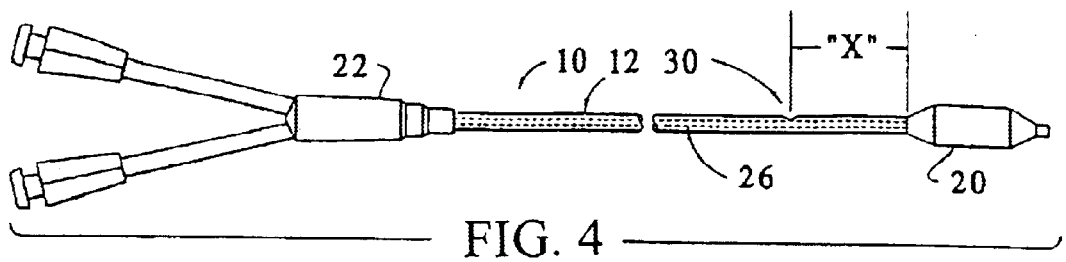
FIG. 4 is a side-elevational view of a catheter assembly showing a bifucated connector therewith.

Referring to the drawings now in detail, and particularly to FIG. 1, there is shown the distal portion of a catheter assembly 10, also shown in its extendedmost form in FIG. 4. The catheter assembly 10 comprises an extruded catheter shaft 12 having a plurality of lumens disposed axially therethrough. The catheter shaft 12 has a first lumen 14, and a second lumen 16, both of which are preferably, but not necessarily of cresent shape, as shown in the cross-sectional view of FIG. 2. The catheter shaft 12 also includes a third lumen 18, which is preferably of circular cross-section.

The catheter shaft 12 has an elongated balloon 20 disposed about its distalmost end, in a known manner. The first lumen 14 extends from an opening, not shown, in a connector 22, shown in FIG. 4, distally towards a closed end 24, at the proximal end of the balloon 20. A stiffening mandrel 26, as shown in FIG. 1, is disposed within the length of the first lumen 14. The stiffening mandrel 26 may have a ball welded tip 28 or be otherwise tapered and flexible on its distalmost end, to prevent puncture of the lumen 14 by the mandrel 26.

The second lumen 16 extends from the connector 22, through the shaft 12, parallel to the first lumen 14, except that the second lumen 16 is in fluid communication with the balloon 20, as shown in phantom lines 17, in FIG. 1. The second lumen 16 provides a conduit for pressurized fluid for inflating and deflating the balloon 20 from an inflation/deflation device, not shown, which would be adaptable to the connector 22. It is to be noted that the view of FIG. 1 is sectioned to show the first lumen 14 and the third lumen 18, and not longitudinally bisect the web of material 19 separating the first and second lumens 14 and 16.

The third lumen 18, of generally circular cross-section, extends from the connector 22, through the shaft 12, and through the balloon 20, opening distally of the balloon 20, as shown in FIGS. 1 and 1A. The third lumen 18 is not in fluid communication with the balloon 20.

An opening or side orifice 30 is disposed through the wall of the catheter shaft 12, and into the third lumen 18, as shown in FIG. 1. The side opening 30 in this preferred embodiment is preferably a slightly oval opening of about 3 mm long and 0.5 mm wide, arranged at a sharp angle "A" of about 20 to about 60 degrees with respect to the longitudinal axis of the shaft. The side opening 30 includes a valve-like cover flap 32, integral with the shaft 12 with a distally tapering edge 33, the flap 32 being about the size to cover the opening 30, and is resilient so as to allow it flex over the opening 30, and within the third lumen 18, obstructing it somewhat, depending upon how the flap 32 is being biased. The side opening 30 is disposed a distance "x" of about 15 to about 35 cm. from the proximal end of the inflated balloon 20, as shown in FIGS. 1 and 4. The third or "distal" lumen 18 may thus be utilized in its entire length, from the proximal connector 22 to its distalmost orifice, for receiving a guidewire in an "over-the-wire" mode, the flap 32 roughly covering the inside of the opening 30. The lumen 18 may also be utilized, from the opening 30 to its distal end, in a "rapid-exchange-wire" mode with a guidewire extending through the distal end of the third lumen 18 and out the opening 39 once the flap 32 is flexed out of the way.

An RO (radio opaque) marker band 34 is disposed about the catheter shaft 12, (essentially the structure comprising the third lumen 18), at the mid-point of the balloon 20 in either the "over-the-wire" mode or the "rapid-exchange" mode.

Figure 6:
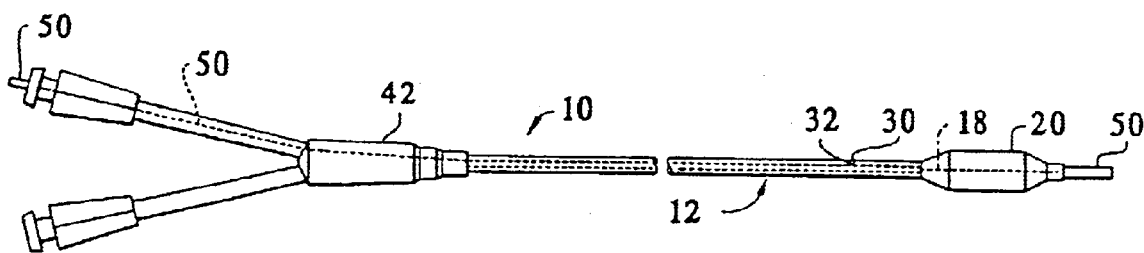
FIG. 6 is a side-elevational view of the catheter assembly in an "over-the-wire" mode.

In one embodiment of the present invention, where the catheter assembly 10 is utilized as aforementioned in the traditional "over-the-wire" catheter, a guidewire 50, normally initially having been inserted into a patient's vessel, and having its proximal end outside of the patient, has that proximal end inserted through the distal end of the catheter assembly 10, through the "distal" or third lumen 18, and it extends proximally, out of the proximal guidewire connector 42, as shown in FIG. 6. The flap 32 performs basically like a valve, by shutting itself against the opening 30, thus permitting an unobstructed lumen for passage of the guidewire 40, or for passage of pressurized fluid injected proximally in the lumen 18 to pass through the lumen 18, to escape primarily out of the distal end of the catheter shaft 12 through the lumen 18.

Figure 7:
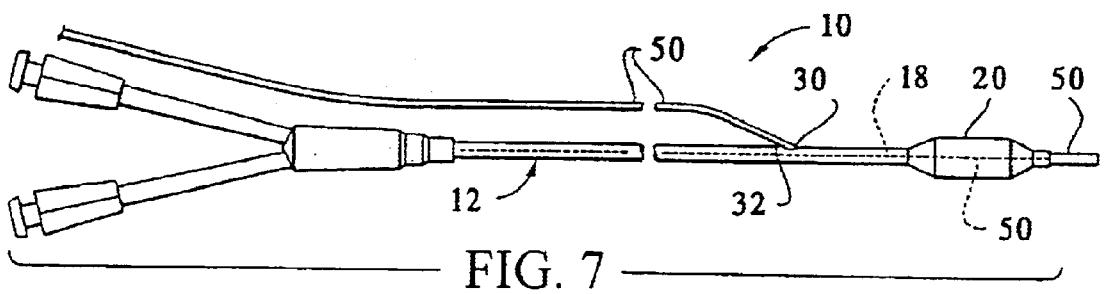
FIG. 7 is a side-elevational view of the catheter assembly in a "rapid exchange mode" configuration.

In a further embodiment of the present invention, where the cateter assembly 10 may be utililized in the aforementioned "rapid-exchange" mode, the guidewire 50, normally initially inserted into a patient's vessel, and having its proximal end outside of the patient, has that proximal end inserted through the distal end of the catheter assembly 10, through the "distal" lumen 18, and extending outwardly proximally, through the side opening 30 as shown in FIGS. 1 and 7. The guidewire 50 in this mode, extends parallel to and external of the shaft 12, proximal of the side opening 30. The enlarged view in FIG. 1A depicts the guidewire 50 shown in phantom lines, and the flap 32 in close fitting overlapping relationship to the guidewire 50. During the threading of the guidewire through the distal lumen 18, it is anticipated that the shaft 12 would be bent into a "U" shape at the opening 30, with the opening 30 in the trough of the "U", so as to cause the flap 32 to bend "away" from the opening 30, obstructing the lumen 18 proximally therepast to permit the guidewire 50 to be threaded through the lumen 18 and out the opening 30.

Additionally, when the catheter assembly 10 is utilized in this "rapid-exchange" mode, a stiffening stylet 52 may be inserted within the "distal" or third lumen 18 through the connector 22, as shown in FIGS. 1, 1A and 2. The stiffening stylet 52 has a distal end 54 which would extend only up to the side opening 30, and no further. The stiffening stylet 52 may have several different configurations, such as shown in FIGS. 3A, 3B or 3C. The stylet 52 shown in FIG. 3A, is a straight mandrel 54, having uniform diameter along its entire length. The stylet 52 shown in FIG. 3B, is a tapered mandrel 56, having an initial diameter (its non-tapered end) of about 0.20 inches, and tapering about 5 cm. or more along its distal length 57 to a diameter of about 0.008 inches. The stylet 52 shown in FIG. 3C is a tapered mandrel 58, similar to the mandrel 56 shown in FIG. 3B, but having a ball weld 60 therein, of a diameter of about 0.020 inches. Each stylet 52 may be made from a stainless steel or Nitinol material, in a known manner.

Figure 5:
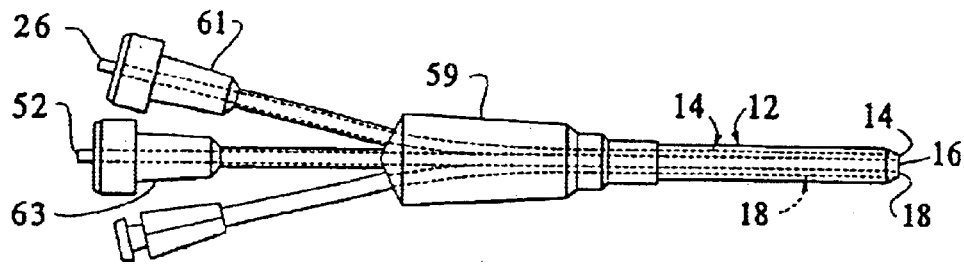
FIG. 5 is a side-elevational view of the proximal end of the catheter assembly showing a trifurcated connector therewith.

It is critical to the present invention that the location of the distalmost end of the stiffening mandrel 26 emplaced within the first lumen 14, as shown in FIG. 1 be juxtaposed distal to the location of the side hole 30 in the distal lumen 18 of the shaft 12. FIG. 5 shows a trifurcated connector 59 mounted on the proximal end of a catheter shaft 12 having a locking hub 61 which would be arranged to adjustably lock at stiffening stylet 26 within the first lumen 14 if desired. A further locking hub 63 may be arranged off of the connector 59 to adjustably seize a stiffening mandrel 52 in the third lumen 18 for longitudinal adjustment thereof, at the physicians option, while the catheter is being utilized in the "rapid-exchange" mode.

Figure 8:
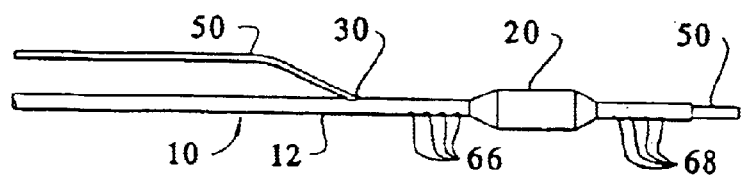
FIG. 8 is a side-elevational view of the catheter assembly in a further embodiment thereof.

FIG. 8 shows a further adaptation of the catheter assembly 10, wherein a plurality of orificii 66 is disposed through the wall of the catheter sheath 12 to provide fluid communication with the distal lumen 18 from the outside of the catheter shaft 12 at a location proximal of the balloon 20, and distal of the side hole 30. The orificii 66 are about 0.025 inches in diameter, and function as openings for passive perfusion. A further similar plurality of orificii 68 is disposed through the wall of the sheath 12 and distal of the balloon 20, to provide fluid communication with the distal lumen 18, to function as openings for passive perfusion with respect to that lumen 18.

Figure 9:
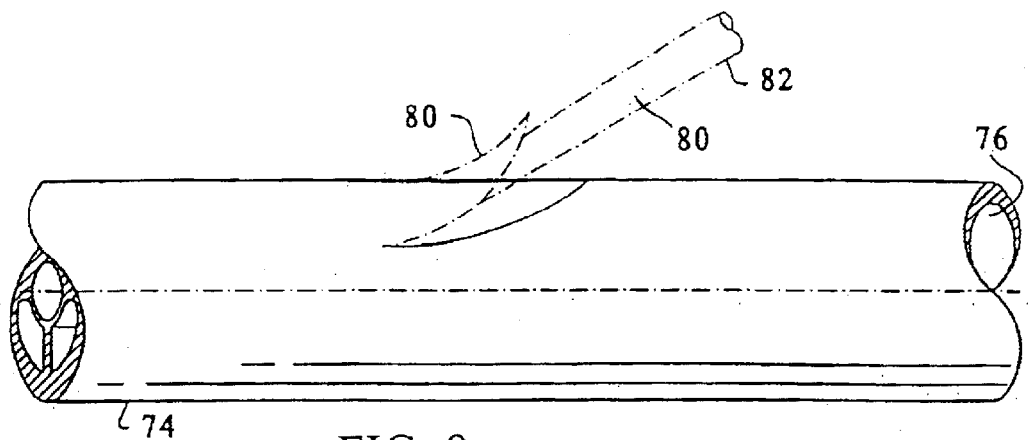
FIG. 9 is a side view of a part of a catheter shaft, in a further embodiment of the side opening.
Figure 10:
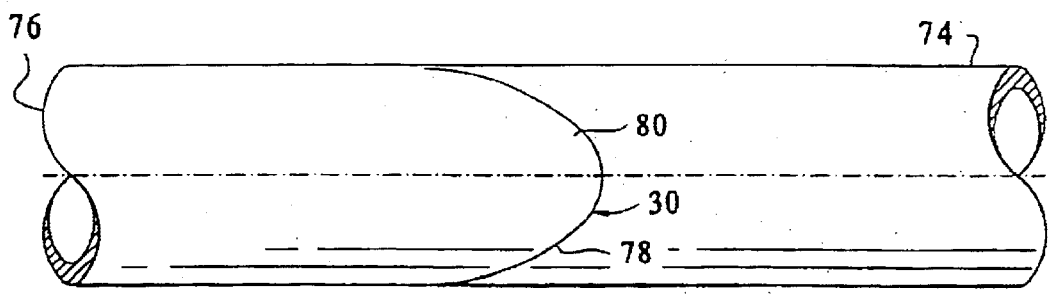
FIG. 10 is a plan view of the opening shown in FIG. 9.

A further embodiment of the side hole 30 is shown in FIG. 9, wherein a portion of a catheter shaft 74 has a "distal" lumen 76 extending therethrough, in a manner similar to the aforementioned catheter shaft 12. A slit 78 is cut diagonally through the outer wall of the catheter shaft 74, making a flap 80, which when flexibly lifted away from the lumen 76 provides a "D" shaped opening, through which a guidewire 82 may be passed. FIG. 10 shows the flap 80 in its "at rest" configuration, with the "D" shaped opening closed, to provide a full passage lumen 76 thereadjacent.

Figure 11:
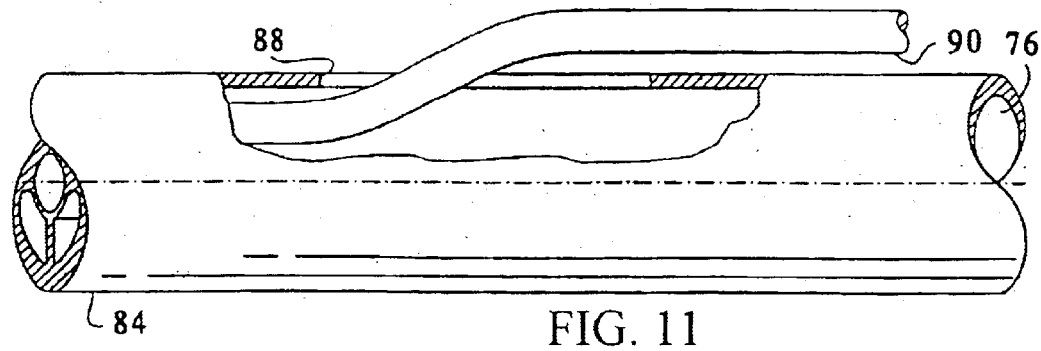
FIG. 11 is a side view of part of a catheter shaft in yet a further embodiment of the side opening.
Figure 12:
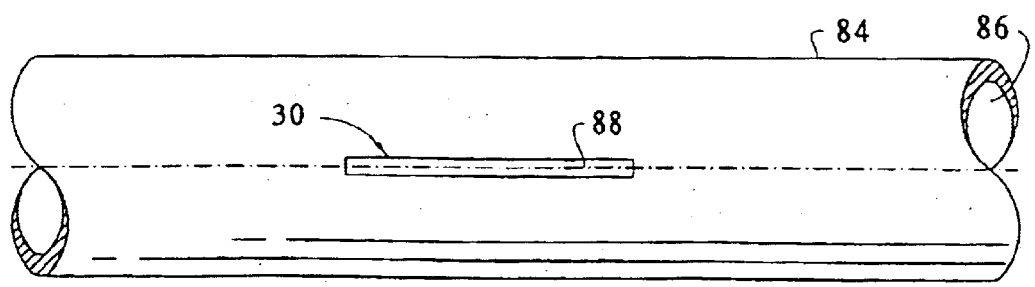
FIG. 12 is a plan view of the opening shown in FIG. 11.

A yet another embodiment of the side hole 30 is shown in FIG. 11, wherein a portion of a catheter shaft 84 has a "distal" lumen 86 extending therethrough. A slot 88 about 2 cm. long and 0.05 cm wide is diposed longitudinally through the outer wall of the catheter shaft 84, to make a flexibly openable orifice which a guidewire 90 may be passed. FIG. 12 shows the slot 38 in a plan view, in its "at rest" configuration.

Thus what has been shown is a novel stiffened catheter assembly 10 capable of being utilized by a physician as an "over-the-wire" catheter with adjustable stiffness means therewith, or optionally as a "rapid-exchange-wire" catheter apparatus, also including the capability of being able to control or vary the stiffness of the catheter shaft by selective insertion and/or controlled withdrawal of a stiffening stylet adaptably arranged within the guidewire lumen, the "rapid-exchange-wire" mode being facilitated by a side opening having valve-like obstructable flap across its inner side to minimize fluid exchange when that lumen accepts the catheter to be utilized in its full length "over-the wire" mode. In its use as either a "rapid-exchange-wire" or an "over-the-wire" mode, the portion of the "distal" lumen enclosing the guidewire may have a plurality of orificii through the wall of the catheter shaft just proximal and just distal of the elongated inflated balloon, to permit perfusion of body fluid across the then expanded balloon in the body vessel.

We claim:

1. A readily exchangeable dilatation catheter suitable for performing angioplasty procedures within a patient's artery, comprising:
    a) an elongated catheter body having proximal and distal ends, a first lumen adapted to receive a guidewire and extending within the catheter body to the distal end thereof and a second lumen adapted to direct inflation fluid therethrough and extending within the catheter body to a distal portion thereof;
    b) an inflatable member on a distal portion of the catheter body having an interior in fluid communication with the second lumen;
    c) a first guidewire port in the catheter body being located at or near the proximal end of the catheter body and being in communication with the guidewire-receiving inner lumen;
    d) a second guidewire port in the catheter body being spaced at least 15 cm from the proximal end of the inflatable member that is on the distal portion of the catheter body and a substantial distance from the proximal end of the catheter body and being in communication with the first guidewire-receiving inner lumen;
    e) a third guidewire port in the distal end of the catheter body distal to the inflatable member which is in communication with the guidewire-receiving inner lumen; and
    f) means on the proximal end of the catheter body to direct inflation fluid to the interior of the inflatable member through the inflation lumen.

2. The catheter of claim 1, wherein said second guidewire port is spaced about 15 to 35 cm from the proximal end of said inflatable member.

* * * * *